(12) United States Patent
Floeder et al.

(10) Patent No.: US 9,142,023 B2
(45) Date of Patent: Sep. 22, 2015

(54) MAINTAINING REGISTRATION OF SPATIALLY SYNCHRONIZED DATA FOR WEB PRODUCTS

(71) Applicant: 3M INNOVATIVE PROPERTIES COMPANY, St. Paul, MN (US)

(72) Inventors: Steven P. Floeder, Shoreview, MN (US); Carl J. Skeps, Lakeville, MN (US); James A. Masterman, Lake Elmo, MN (US); Matthew V. Rundquist, Woodbury, MN (US)

(73) Assignee: 3M INNOVATIVE PROPERTIES COMPANY, St. Paul, MN (US)

( * ) Notice: Subject to any disclaimer, the term of this patent is extended or adjusted under 35 U.S.C. 154(b) by 0 days.

(21) Appl. No.: 14/366,791

(22) PCT Filed: Dec. 19, 2012

(86) PCT No.: PCT/US2012/070524
§ 371 (c)(1),
(2) Date: Jun. 19, 2014

(87) PCT Pub. No.: WO2013/096397
PCT Pub. Date: Jun. 27, 2013

(65) Prior Publication Data
US 2014/0369591 A1    Dec. 18, 2014

Related U.S. Application Data

(60) Provisional application No. 61/579,335, filed on Dec. 22, 2011.

(51) Int. Cl.
| | |
|---|---|
| *G06K 9/62* | (2006.01) |
| *G06T 7/00* | (2006.01) |
| *D06H 3/08* | (2006.01) |
| *G01N 21/89* | (2006.01) |
| *G06F 17/30* | (2006.01) |

(52) U.S. Cl.
CPC ........ *G06T 7/004* (2013.01); *D06H 3/08* (2013.01); *G01N 21/89* (2013.01); *G06F 17/30244* (2013.01); *G06T 2207/30124* (2013.01)

(58) Field of Classification Search
None
See application file for complete search history.

(56) References Cited

U.S. PATENT DOCUMENTS

| | | |
|---|---|---|
| 3,403,782 A | 10/1968 | Schafer |
| 7,542,821 B2 | 6/2009 | Floeder |

(Continued)

FOREIGN PATENT DOCUMENTS

WO     2005-106104     11/2005

OTHER PUBLICATIONS

International Search Report PCT International Application No. PCT/US2012/070524 mailed on Mar. 13, 2013, 3 pages.

*Primary Examiner* — Brian P Werner
(74) *Attorney, Agent, or Firm* — Robert H. Jordan (57) ABSTRACT

Techniques are described for maintaining synchronization of inspection data when a web roll is converted into intermediate smaller rolls prior to cutting the web into individual parts. A system comprises a database that stores anomaly data acquired from a manufactured web. The anomaly data specifies positions anomalies within a manufactured web relative to a set of fiducial marks on the manufactured web. A conversion processing line comprises a fiducial mark reader to output position information for the set of fiducial marks on the manufactured web, a slitter that cuts the manufactured web into slit rolls, and a fiducial mark printer to print a set of fiducial marks on each slit roll. A position monitoring system maintains spatial synchronization of the anomaly data by computing an updated position for the anomalies relative to the set of fiducial marks printed on the slit rolls.

16 Claims, 8 Drawing Sheets

(56) References Cited

U.S. PATENT DOCUMENTS

| | | | |
|---|---|---|---|
| 7,623,699 B2 * | 11/2009 | Floeder et al. | 382/149 |
| 2006/0090319 A1 * | 5/2006 | Howe | 29/407.05 |
| 2009/0030544 A1 * | 1/2009 | Floeder et al. | 700/122 |
| 2010/0063750 A1 | 3/2010 | Floeder | |
| 2011/0224918 A1 | 9/2011 | Floeder | |

* cited by examiner

MAINTAINING REGISTRATION OF SPATIALLY SYNCHRONIZED DATA FOR WEB PRODUCTS

TECHNICAL FIELD

The present invention relates to automated inspection of systems, and more particularly, to inspection of continuously moving webs.

BACKGROUND

Inspection systems for the analysis of moving web materials have proven critical to modern manufacturing operations. Industries as varied as metal fabrication, paper, non-wovens, and films rely on these inspection systems for both product certification and online process monitoring. One major difficulty in the industry is related to the extremely high data processing rates required to keep up with current manufacturing processes. With webs of commercially viable width and web speeds that are typically used and pixel resolution that is typically needed, data acquisition speeds of tens or even hundreds of megabytes per second are required of the inspection systems. It is a continual challenge to process images and perform accurate defect detection at these data rates.

SUMMARY

In general, techniques are described for maintaining spatial synchronization of inspection data of manufactured webs. For example, a system is described that performs spatial registration of anomaly data (e.g., defects or potential defects) collected throughout the production of a web. The techniques maintain spatial synchronization of the anomaly data even though the web may be subjected to a multi-stage converting process in which larger web rolls are converted into smaller rolls and ultimately into individual parts. The techniques may allow a saleable roll (e.g., an individual split roll) or an individual part to be traced back to the particular manufacturing conditions or quality information gathered during original manufacturing.

In one embodiment, a method comprises storing anomaly data that specifies a position of at least one anomaly within a first web relative to a set of fiducial marks on the first web. The method further comprises registering, with a fiducial mark reader, position information for the set of fiducial marks on the first web, and cutting, with a slitter positioned downweb from the fiducial mark reader, the first web into two or more slit rolls of web material. The method further comprises controlling a fiducial mark printer downweb from the slitter to print a set of fiducial marks on the web material of each of the slit rolls based on the position information for the set of fiducial marks on the first web, and maintaining spatial synchronization of the anomaly data with a position monitoring system by computing an updated position for the anomaly relative to the set of fiducial marks printed on the web material of the slit rolls.

In another embodiment, a system comprises a database that stores anomaly data acquired from a manufactured web, wherein the anomaly data specifies a position of at least one anomaly within a manufactured web relative to a set of fiducial marks on the manufactured web. A conversion processing line comprises a fiducial mark reader to output position information for the set of fiducial marks on the manufactured web, a slitter positioned downweb from the fiducial mark reader to cut the manufactured web into two or more slit rolls of web material, and a fiducial mark printer to print a set of fiducial marks on the web material of each of the slit rolls. A position monitoring system maintains spatial synchronization of the anomaly data by computing an updated position for the anomaly relative to the set of fiducial marks printed on the web material of the slit rolls.

The details of one or more embodiments of the invention are set forth in the accompanying drawings and the description below. Other features, objects, and advantages of the invention will be apparent from the description and drawings, and from the claims.

DEFINITIONS

For purposes of the present invention, the following terms used in this application are defined as follows:

"web" means material having a fixed dimension in one direction ("crossweb direction") and either a predetermined or indeterminate length in the orthogonal direction ("downweb direction");

"defect" means an undesirable occurrence in a product;

"anomaly" or "anomalies" mean a deviation from normal product that may or may not be a defect, depending on its characteristics and severity;

"products" are the individual sheets (also referred to as component) produced from a web, e.g., a rectangular sheet of film for a cell phone display or a television screen;

"conversion" is the process of physically cutting a web into products; and a "jumbo roll" is any roll of web material that is processed into two or more smaller rolls ("slit rolls") prior to converting to products, e.g., by cutting the web material of the jumbo roll at one or more cross-web positions.

DETAILED DESCRIPTION

Figure 1:
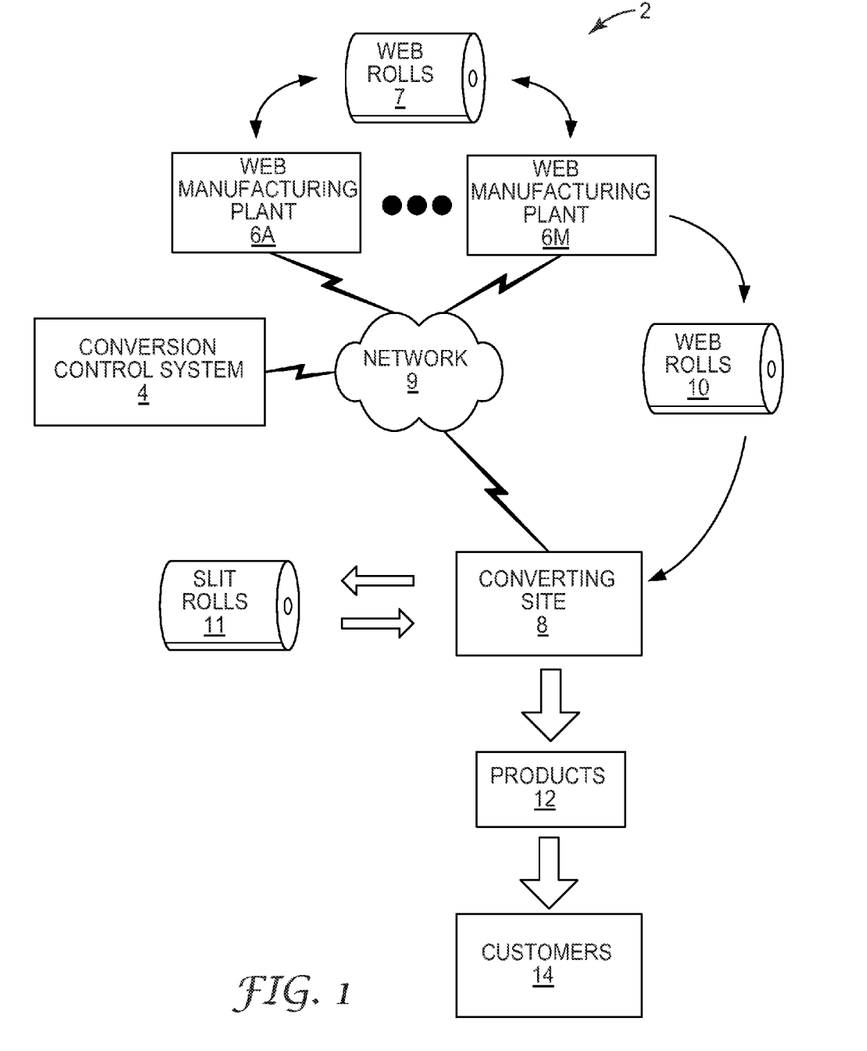
FIG. 1 is a block diagram illustrating a global network environment in which a conversion control system controls conversion of web material.
Figure 3:
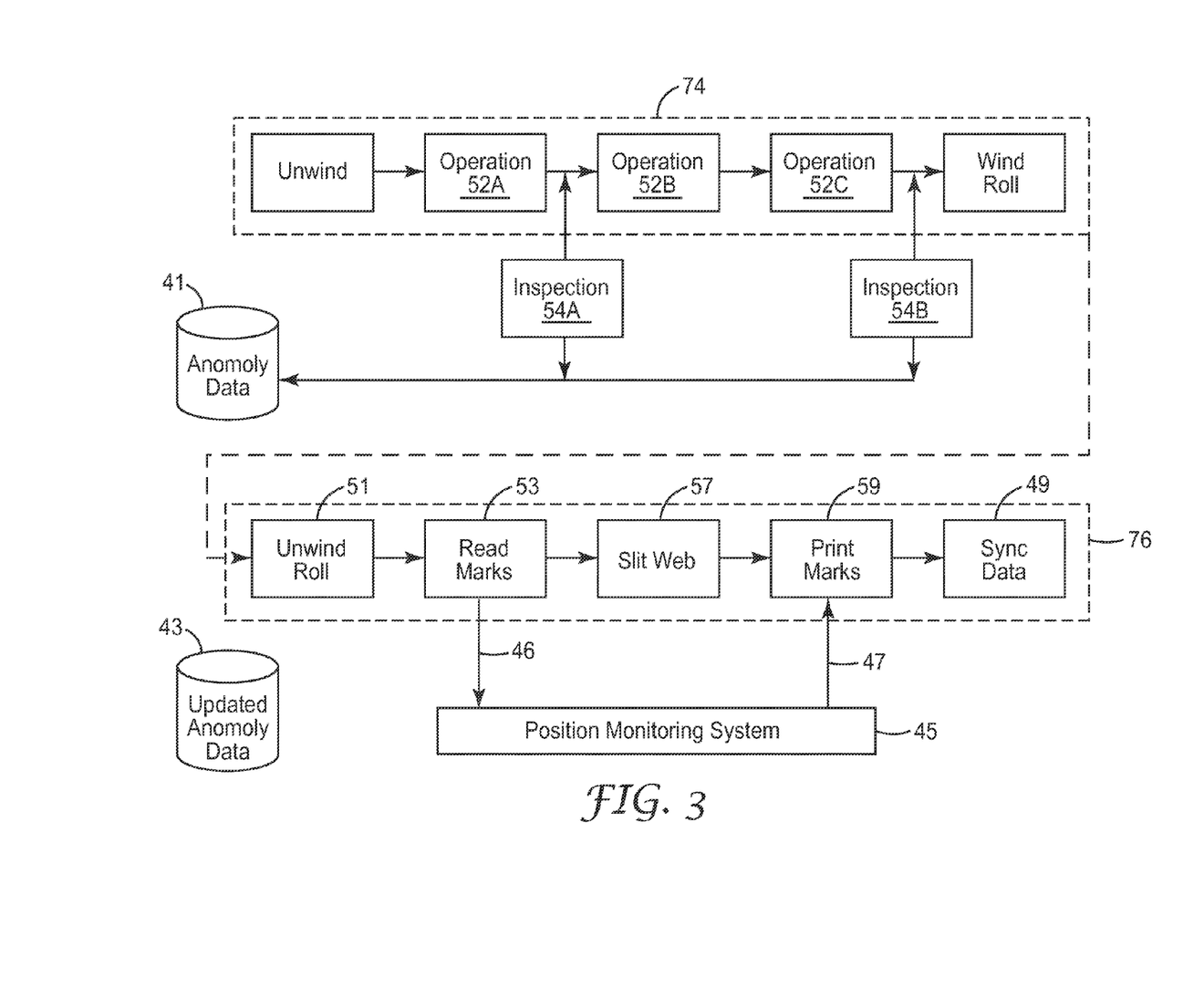
FIG. 3 is a block diagram illustrating an exemplary sequence of procedures and inspections for a web.

FIG. 1 is a block diagram illustrating a global network environment 2 in which conversion control system 4 controls conversion of web material. More specifically, web manufacturing plants 6A-6M ("web manufacturing plants 6") represent manufacturing sites that produce and ship web material in the form of web rolls 7 between each other and ship finished web rolls 10 to converting sites 8A-8N (a single converting site 8 is shown). Web manufacturing plants 6 may be geographically distributed, and each of the web manufacturing plants may include one or more manufacturing process lines (FIG. 3).

In general, web rolls 7 may contain manufactured web material that may be any sheet-like material having a fixed dimension in one direction and either a predetermined or indeterminate length in the orthogonal direction. Examples of web materials include, but are not limited to, metals, paper, wovens, non-wovens, glass, polymeric films, flexible circuits or combinations thereof. Metals may include such materials as steel or aluminum. Wovens generally include various fabrics. Non-wovens include materials, such as paper, filter media, or insulating material. Films include, for example, clear and opaque polymeric films including laminates and coated films.

In order to manufacture a finished web roll 10 which is ready for conversion into products 12, unfinished web rolls 7 may need to undergo processing from multiple process lines either within one web manufacturing plant, for instance, web manufacturing plant 6A, or within multiple manufacturing plants. For each process, a web roll is typically used as a source roll from which the web is fed into the manufacturing process. After each process, the web is typically collected again into a web roll 7 and moved to a different product line or shipped to a different manufacturing plant, where it is then unrolled, processed, and again collected into a roll. This process is repeated until ultimately a finished web roll 10 is produced.

For many applications, the web materials for each of web rolls 7 may have numerous coatings applied at one or more production lines of one or more web manufacturing plants 6. The coating is generally applied to an exposed surface of either a base web material, in the case of the first manufacturing process, or a previously applied coating in the case of a subsequent manufacturing process. Examples of coatings include adhesives, hardcoats, low adhesion backside coatings, metalized coatings, neutral density coatings, electrically conductive or nonconductive coatings, or combinations thereof. A given coating may be applied to only a portion of the web material or may fully cover the exposed surface of the web material. Further, the web materials may be patterned or unpatterned.

Figure 2:
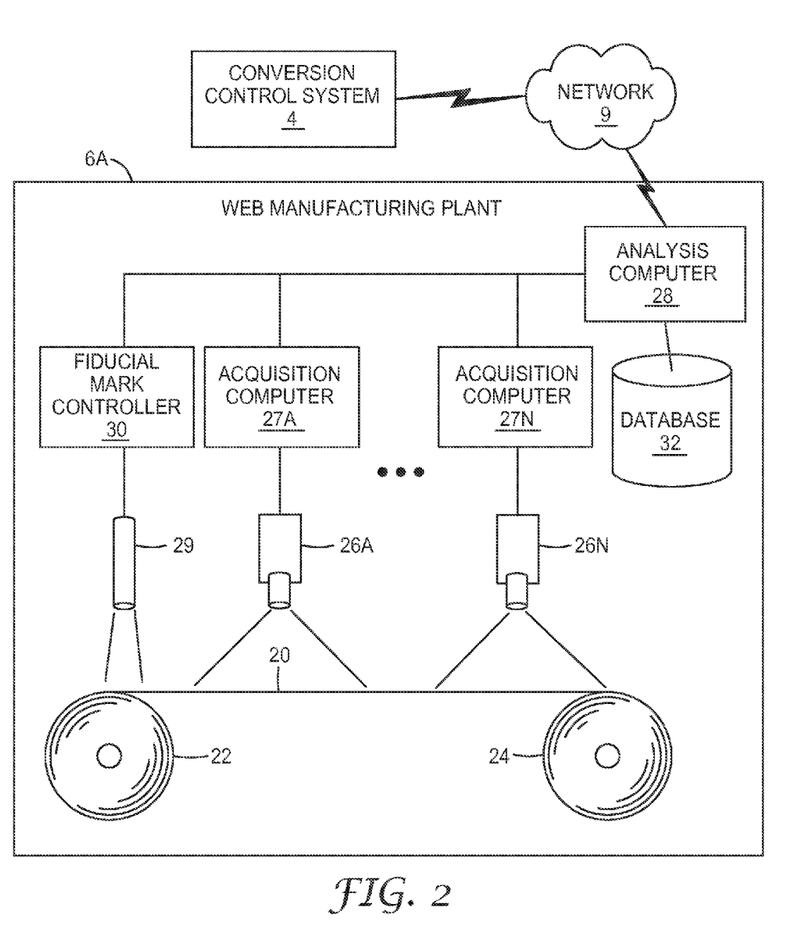
FIG. 2 is a block diagram illustrating an exemplary embodiment of a web manufacturing plant.

During each manufacturing process for a given one of web rolls 7, one or more inspection systems acquire anomaly information for the web. For example, as illustrated in FIG. 2, an inspection system for a production line may include one or more image acquisition devices positioned in close proximity to the continuously moving web as the web is processed, e.g., as one or more coatings are applied to the web. The image acquisition devices scan sequential portions of the continuously moving web to obtain digital image data. The inspection systems may analyze the image data with one or more algorithms to produce so called "local" anomaly information. The anomaly information may be referred to herein as local anomaly information in that the anomaly information generally includes position information that is specific to a coordinate system local to, or generally used by, the production line currently in use. As described below, this local position information may be meaningless to other manufacturing plants or even other production lines within the same manufacturing plant. For these reasons, the local anomaly information obtained during the production for each of web rolls 7 is spatially registered with other local anomaly information for the same web roll. That is, the position information associated with the local anomaly is translated to a common coordinate system to align position information from different manufacturing processes applied to the same web roll 7 or a segment of web roll 7. The anomaly information is referred to herein as "aggregate" anomaly information once collected and aligned with anomaly information for at least one or possibly all of the manufacturing processes for the same web roll 7.

More specifically, during each manufacturing process, the image information (i.e., raw pixel information) for any regions of the web containing anomalies is stored for subsequent processing. That is, the raw image data surrounding an identified anomaly is extracted from the stream of pixel information obtained from the image acquisition device and stored along with position information indicating the specific location of the anomaly within the web, both with respect to the dimension across the web and the dimension running the length of the web. Image data not associated with anomalies is discarded. Similar techniques are applied at each process within the multi-process production of a given web roll 7, thereby generating local anomaly information for each of the manufacturing processes, i.e., stages.

The local anomaly information generated during the various production processes for the moving web is then communicated to conversion control system 4, where the local anomaly information from the different processes for the web can be spatially registered. That is, the respective anomaly information from the different processes can be aligned such that the anomalies from the different manufacturing processes have spatial relevance with each other to produce the aggregate anomaly information for a given web roll 7. Spatial registration may occur at any time during the overall manufacturing process, e.g., between each stage of the multi-process production for a web roll or after completion of all the processes. Moreover, spatial registration may be performed centrally, such as within conversion control system 4, or locally at a given web manufacturing plant 6 using the local anomaly information obtained from the production lines previously used for the given web roll 7.

In general, conversion control system 4 applies one or more defect detection algorithms that may be application-specific, i.e., specific to products 12, to select and generate a conversion plan for each web roll 10. A certain anomaly may result in a defect in one product, for instance product 12A, whereas the anomaly is not a defect in a different product, for instance, product 12B. Each conversion plan represents defined instructions for processing a corresponding finished web roll 10. Conversion control system 4 communicates the conversion plans for web rolls 10 via network 9 to the appropriate converting sites 8 for use in converting the web rolls into products 12.

In order to properly create a conversion plan for converting a finished web roll 10 which has undergone multiple manufacturing processes, the data collected by web manufacturing plants 6 is spatially reconciled and analyzed to form a composite defect map. As noted above, collected anomaly data generally includes small regions of raw image data along with position information representing the locations of anomalies on a web roll. Spatial reconciliation of anomaly data can either be done at a central location, such as conversion control system 4, once all processes have finished or at various intermediate process locations. Moreover, a predefined, spatial coordinate system may be used for registration of the data. In this case, all of the position data associated with the local anomaly information is translated to this predefined coordinate system. As an alternative, a coordinate system used within a first process (or any other process) applied to a given web roll 7 can act as a reference coordinate system to which all local anomaly data is registered for subsequent processes applied to the same web roll.

For example, an inspection system for a first manufacturing process applied to a given web roll 7 can submit its local anomaly information to conversion control system 4 once the first process has finished. This may include coordinate system reference data describing a coordinate system utilized by the inspection system while collecting the initial local anomaly information. Then, inspection systems or other computing devices associated with each subsequent manufacturing process applied to that same web roll 7 may retrieve the coordinate system reference data used by the first process from conversion control system 4 and adjust the position data for any newly gathered local anomaly information according to the coordinate system used during the first manufacturing process. As mentioned, alternatively, conversion control system 4 may process local anomaly information from each of the manufacturing processes. In this manner, all of the position data of the local anomaly information gathered from all manufacturing processes for the same web roll 7 can be reconciled so that all anomalous regions in web roll 10 are known regardless of when, that is, from which process, each anomaly was introduced.

Conversion control system 4 applies one or more defect detection algorithms to the aggregate anomaly information to ultimately select and generate a conversion plan for each web roll 10. Conversion control system 4 may select converting sites 8 based on one or more parameters, and ultimately may direct the conversion of web rolls 10 into products 12. That is, conversion control system 4 selects, in an automated or semi-automated manner, converting sites 8 for converting web rolls 10 based on one or more site selection parameters, such as current product inventory levels at the various converting sites. Conversion control system 4 may utilize other site selection parameters, such as order information associated with each of products 12 at the various converting sites 8, current product demand experienced within the geographic regions serviced by the converting sites, shipping costs and transportation options associated with each of the converting sites, and any time-critical orders pending at the converting sites.

Based on the selections made by conversion control system 4, web rolls 10 are shipped to converting sites 8A-8N ("converting sites 8"), which may be geographically distributed within different countries. Converting sites 8 convert each web roll 10 into one or more products. Specifically, each of converting sites 8 includes one or more process lines that physically cut the web for a given web roll 10 into numerous individual sheets, individual parts, or numerous web rolls, referred to as products 12A-12N ("products 12"). As one example, converting site 8A may convert web rolls 10 of film into individual sheets for use in automobile lighting systems. Similarly, other forms of web materials may be converted into products 12 of different shapes and sizes depending upon the intended application by customers 14A-14N ("customers 14"). Each of converting sites 8 may be capable of receiving different types of web rolls 10, and each converting site may produce different products 12 depending on the location of the converting site and the particular needs of customers 14.

In some cases, in order to convert web roll 10 into products 12, each of web rolls 10 may undergo processing from an initial web roll (also referred to as a "jumbo" roll) into two or more smaller ("slit") rolls 12. That is a web roll 10 may be cut lengthwise into two or more slit rolls 11 that may be separately processed into products 12. The operations of producing slit rolls 11 from web rolls 10 may occur within converting sites 8 (as shown in the example of FIG. 1) or individually either within web manufacturing plants 6 or converting sites 8.

The techniques described herein maintain spatial synchronization of anomaly data that was originally obtained from manufactured webs 7, 10. For example, a system is described that performs spatial registration of anomaly data (e.g., defects or potential defects) collected throughout the production of a web. The techniques maintain spatial synchronization of the anomaly data even though the web may be subjected to a multi-stage converting process in which larger web rolls are converted into smaller rolls and ultimately into individual parts. That is, the techniques allow the anomaly data originally collected from web rolls 7 or 10 to be re-registered with position information specific to slit rolls 11.

The ability to re-register slit rolls 11 with anomaly information acquired during the manufacture of original web rolls 7 or web rolls 10 may provide many advantages, such as significantly enhanced process quality analysis and control, defective product containment, increased utilization of the web, reduced cost, increased revenue or profit and a variety of other potential benefits. For example, it may be possible to provide a level of automated quality control or rejection on a per-product basis for products 12 produced from individual slit rolls 11 even though the original web roll 7 or 10 for which the anomaly data has been gather has been cut into different slit rolls. The techniques may allow a saleable roll (e.g., an individual split roll 7) or an individual part 12 to be traced back to the particular manufacturing plant 6 and associated with the original anomaly data gathered during original manufacturing.

FIG. 2 is a block diagram illustrating an exemplary embodiment of a process line in an exemplary embodiment of web manufacturing plant 6A of FIG. 1. In the exemplary embodiment, a manufacturing machine positions a segment of a web 20 between two support rolls 22, 24. Image acquisition devices 26A-26N ("image acquisition devices 26") are positioned in close proximity to the continuously moving web 20. Image acquisition devices 26 scan sequential portions of the continuously moving web 20 to obtain image data. Acquisition computers 27 collect image data from image acquisition devices 26, and transmit the image data to analysis computer 28 for preliminary analysis.

Image acquisition devices 26 may be conventional imaging devices that are capable of reading a sequential portion of the moving web 20 and providing output in the form of a digital data stream. As shown in FIG. 2, imaging devices 26 may be cameras that directly provide a digital data stream or an analog camera with an additional analog to digital converter. Other sensors, such as, for example, laser scanners may be utilized as the imaging acquisition device. A sequential portion of the web indicates that the data is acquired by a succession of single lines. Single lines comprise an area of the continuously moving web that maps to a single row of sensor elements or pixels. Examples of devices suitable for acquiring the image include linescan cameras such as Model#LD21 from Perkin Elmer (Sunnyvale, Calif.), Piranha Models or Model ATMEL-AVIIVA SC2 CL, both from Teledyne DALSA (Bellerica, Mass.). Additional examples include laser scanners from Surface Inspection Systems GmbH (Munich, Germany) in conjunction with an analog to digital converter.

The image may be optionally acquired through the utilization of optic assemblies that assist in the procurement of the image. The assemblies may be either part of a camera, or may be separate from the camera. Optic assemblies utilize reflected light, transmitted light, or transflected light during the imaging process. Reflected light, for example, is often suitable for the detection of defects caused by web surface deformations, such as surface scratches.

Fiducial mark controller 30 controls fiducial mark reader 29 to collect roll and position information from web 20. For example, fiducial mark controller may include one or more photo-optic sensors for reading bar codes or other indicia from web 20. In addition, fiducial mark controller 30 may receive position signals from one or more high-precision encoders engaged with web 20 and/or rollers 22, 24. Based on the position signals, fiducial mark controller 30 determines position information for each detected fiducial mark. For example, fiducial mark controller 30 may produce position information locating each detected fiducial mark within a coordinate system applied to the process line. Alternatively, analysis computer 28 may place each of the detected fiducial marks within the coordinate system based on the position data received from fiducial mark controller 30. In this case, the position data provided by fiducial mark controller 30 may represent distances between each fiducial mark in a dimension along the length of web 20. In either case, fiducial mark controller 30 communicates the roll and position information to analysis computer 28.

Analysis computer 28 processes image streams from acquisition computers 27. Analysis computer 28 processes the digital information with one or more initial algorithms to generate local anomaly information that identifies any regions of web 20 containing anomalies that may ultimately qualify as defects. For each identified anomaly, analysis computer 28 extracts from the image data an anomaly image that contains pixel data encompassing the anomaly and possibly a surrounding portion of web 20. Analysis computer 28 may classify an anomaly into different defect classes if necessary. For instance, there may be unique defect classes to distinguish between spots, scratches, and oil drips. Other classes may distinguish between further types of defects.

Based the position data produced by fiducial mark controller 30, analysis computer 28 determines the spatial position of each anomaly within the coordinate system of the process line. That is, based on the position data from fiducial mark controller 30, analysis computer 28 determines the x-y and possibly z position for each anomaly within the coordinate system used by the current process line. For example, a coordinate system may be defined such that the x dimension represents a distance across web 20, a y dimension represents a distance along a length of the web, and the z dimension represents a height of the web, which may be based on the number of coatings, materials or other layers previously applied to the web. Moreover, an origin for the x, y, z coordinate system may be defined at a physical location within the process line, and is typically associated with an initial feed placement of the web 20. The coordinate system defined for the current process line may not be (and is typically not) the same coordinate system for any previous or subsequent processes applied to web 20.

In any case, analysis computer 28 records in database 32 the spatial location of each anomaly with respect to the coordinate system of the process line, this information being referred to herein as local anomaly information. That is, analysis computer 28 stores the local anomaly information for web 20, including roll information for the web 20 and position information for each anomaly, within database 32. As described below, the local anomaly information generated for the current process line is subsequently spatially registered with local anomaly information generated by the other process lines for the same web. Database 32 may be implemented in any of a number of different forms including a data storage file or one or more database management systems (DBMS) executing on one or more database servers. The database management systems may be, for example, a relational (RDBMS), hierarchical (HDBMS), multidimensional (MDBMS), object oriented (ODBMS or OODBMS) or object relational (ORDBMS) database management system. As one example, database 32 is implemented as a relational database provided by SQL SERVER from Microsoft Corporation (Redmond, Wash.).

Once the process has ended, analysis computer 28 will transmit the data collected in database 32 to conversion control system 4 via network 9. Specifically, analysis computer 28 communicates the roll information as well as the local anomaly information and respective sub-images to conversion control system 4 for subsequent, offline, detailed analysis. For example, the information may be communicated by way of a database synchronization between database 32 and conversion control system 4.

Spatial registration of anomaly data can be performed subsequently at conversion control system 4, either after one or more processes or once all processes have finished. Alternatively, analysis computer 28 may perform the spatial registration. For example, in such an embodiment, conversion control system 4 may communicate through network 9 with analysis computer 28 to inform analysis computer 28 of a coordinate system that is to be used for reconciled anomaly data. In this case, analysis computer 28 may spatially register local anomaly data for web 20, which is typically based on a coordinate system of the current process line, with the representative coordinate system specified by conversion control system. Conversion control system 4 may select the representative coordinate system that is to be used for spatial registration based on a coordinate system associated with the first manufacturing process line applied to web 20. Alternatively, coordinate system of any other process line used or scheduled to be used for web 20 may be selected. Moreover, conversion control system 4 may define a coordinate system different from any of the coordinate systems associated with the product lines.

As explained herein, the techniques maintain the spatial registration of anomaly data produced by analysis computer 28 throughout the subsequent conversion process of web 20 even though web 20 may be subjected to a multi-stage converting process in which web 20 is cut into smaller rolls (slit rolls 11) and ultimately into individual parts 12. The techniques allow the anomaly data originally collected from web 20 and positionally-registered with the web by analysis computer 28 to be subsequently re-registered with position information specific to slit rolls 11. In this way, the anomaly data may be applied to the web material of slit rolls 11 and products 12, e.g., for quality control and product tracing.

FIG. 3 is a block diagram illustrating an exemplary sequence of manufacturing processes 74 and a conversion processing line 76. In an exemplary embodiment, the sequence of manufacturing processes 74 may perform numerous individual manufacturing processes upon web roll 7. In general, manufacturing process 74 includes a transport system to transport a web through various equipment that performs operations 52 to manufacture web roll 7. At this time, one or more inspection systems perform a number of inspection operations 54 to acquire anomaly data 41 that specifies positions for anomalies within the web material. Typically, anomaly data 41 includes position information that specifies a downweb and crossweb position relative to a first set of fiducial marks that are either pre-existing on the web or applied to the web during manufacturing process 74.

In an exemplary sequence of processes and inspections, such as that depicted in FIG. 3, a web roll 7 may be a plastic film, which may begin on manufacturing process 74A where a base film is first formed in accordance with operation 52A. On this process line, web roll 7 may be unwound and subjected to an initial inspection 54A. Operation 52A may, for example, clean web roll 7, operation 52B may prime web roll 7, and operation 52C may cure web roll 7. Web roll 7 may then be inspected a second time by inspection 54B and then wound into a roll. Web roll 7 may subsequently be moved or shipped to one or more additional process lines, where the web roll may be unwound for feeding into the process line. For example, a process line may be used to impart web roll 7 with an embossed pattern and then an inspection operation 54C is performed before being collected into a roll. Additional manufacturing processes may be performed by subsequent process lines, until web roll 7 is converted. As examples, web roll 7 may be coated with an opaque adhesive, uv-cured laminated with a liner film and rewound into the final form as web roll 10. Web roll 10 is then ready to be converted into products 12 via conversion processing line 76.

Any one of operations 52 may impart anomalies into web roll 7 that are subsequently identified as defects. Therefore, it may be desirable to inspect for defects within one or more of the different manufacturing process lines. By frequently inspecting the web, the local anomaly information captured from the inspections 54 can be examined to individually optimize each of processes 52. This may allow for identification of the causes of defects for expeditious correction. Moreover, local anomaly information captured from each of the inspections 54 can be spatially registered to form aggregate anomaly data 41 that can be used for a variety of purposes. For example, aggregate anomaly data 41 can be examined to further optimize the operations based on their contribution to the overall defects in the end products. That is, depending upon the product application ultimately selected for the web, some of the operations performed by processes 52 may act to eliminate, cover or otherwise act to effectively remove or lessen the effect of an anomaly introduced by a previous one of the processes. An anomaly introduced into a base material of the web, for example, may be subsequently covered by coatings applied to the web. In addition, some so-called hidden anomalies may have little or no impact on the ultimate performance of the end products.

Either while manufacturing the web or during conversion to specific products, the web may be cut into one or more slit rolls 11. Existing anomaly data 41 that has already been spatially registered is preserved and can be re-registered to positional information for the individual slit rolls 11 as updated anomaly data 43. For example, during conversion processing line 76, the web roll is unwound 51 onto a transport system, and position monitoring system 45 receives position information 53 from existing fiducial marks on web roll 10 during the course of processing. Web roll 10 is then processed 57 web into two or more smaller slit rolls 11. Position monitoring system 45 outputs signals to direct one or more fiducial mark printers to print 59 a set of fiducial marks on each individual slit roll. The fiducial mark printer may print the set of fiducial marks on the web material of the slit rolls at substantially the same downweb positions as the set of fiducial marks on the original web roll or at a known downweb offset.

Position monitoring system 45 may compute a position associated with each of the fiducial marks printed on the smaller slit rolls 10 directly from the positional data determined from the existing fiducial marks on the original web roll 10 prior to processing the web roll into individual slit rolls. Slit rolls 11 are associated with anomaly data 41 previously collected for web roll 10. At this time, for example, position monitoring system 45 may recompute a position for each anomalies defined within anomaly data 41 so that the positions of the anomalies are relative to the downweb and crossweb positions of the fiducial marks newly applied to the individual slit rolls 11. In this way, anomaly data 41 of web roll 10 is re-registered and spatially synchronized with the fiducial marks of the smaller rolls as updated anomaly data 43. As a result, automated quality control may be utilized on a per-product basis for products 12 produced from individual slit rolls 11 using the anomaly data originally collected during manufacturing process 74. The techniques may allow a saleable roll (e.g., an individual split roll 7) or an individual part 12 to be traced back to the particular manufacturing plant 6 and associated with the anomaly data gathered during original manufacturing of the jumbo web roll.

Figure 4:
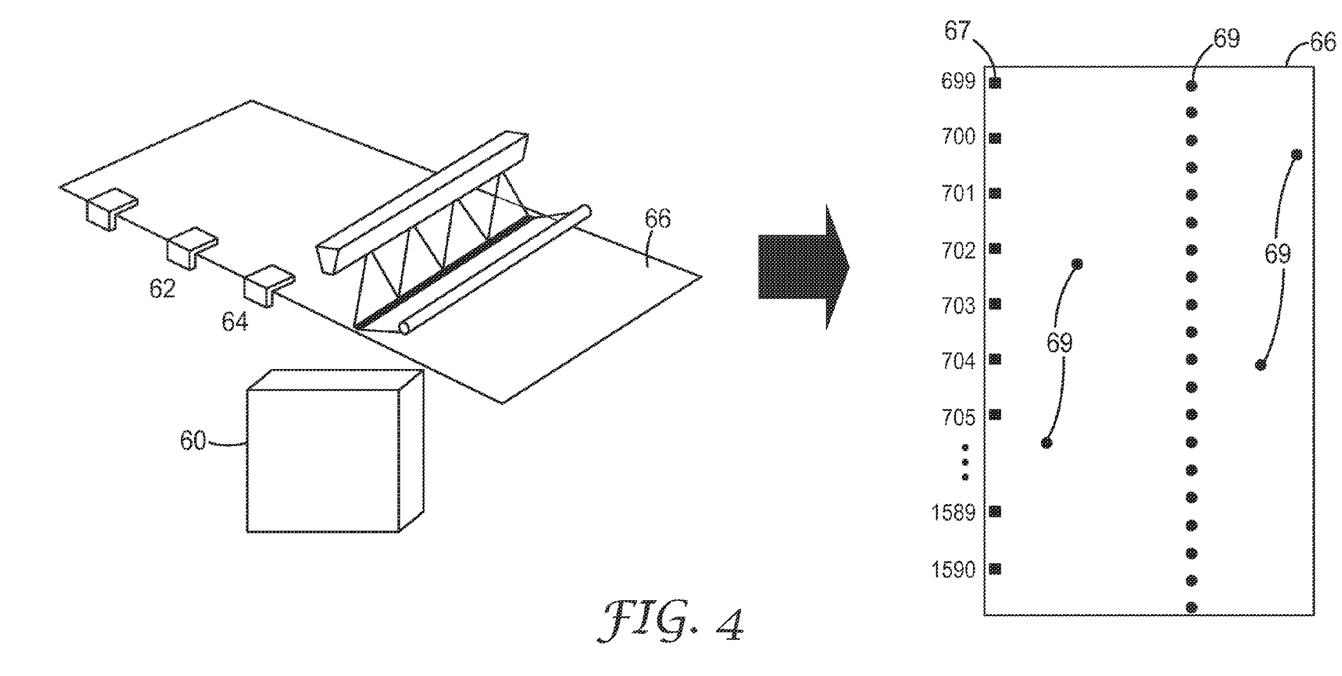
FIG. 4 illustrates example application of fiducial marks in conjunction with an automated inspection system.

FIG. 4 illustrates example application of fiducial marks in conjunction with an automated inspection system 60 during a manufacturing process (e.g., manufacturing process 74). In one example, the physical fiducial marks are applied using an ink-based fiducial mark printer 62 and read using a barcode reader 64, although a variety of other suitable mechanisms may be used. During the course of physical inspection, the positions of the fiducial marks are stored in a production database (e.g., database 32) in conjunction with quality of other manufacturing information. In this case, the position of identified anomalies 69 is determined and registered relative to the position of the fiducial marks 67. At some later time as roll 66 is processed, the position of each anomaly 69 can be determined to a high degree of accuracy by reference to fiducial marks 67.

Figure 5:
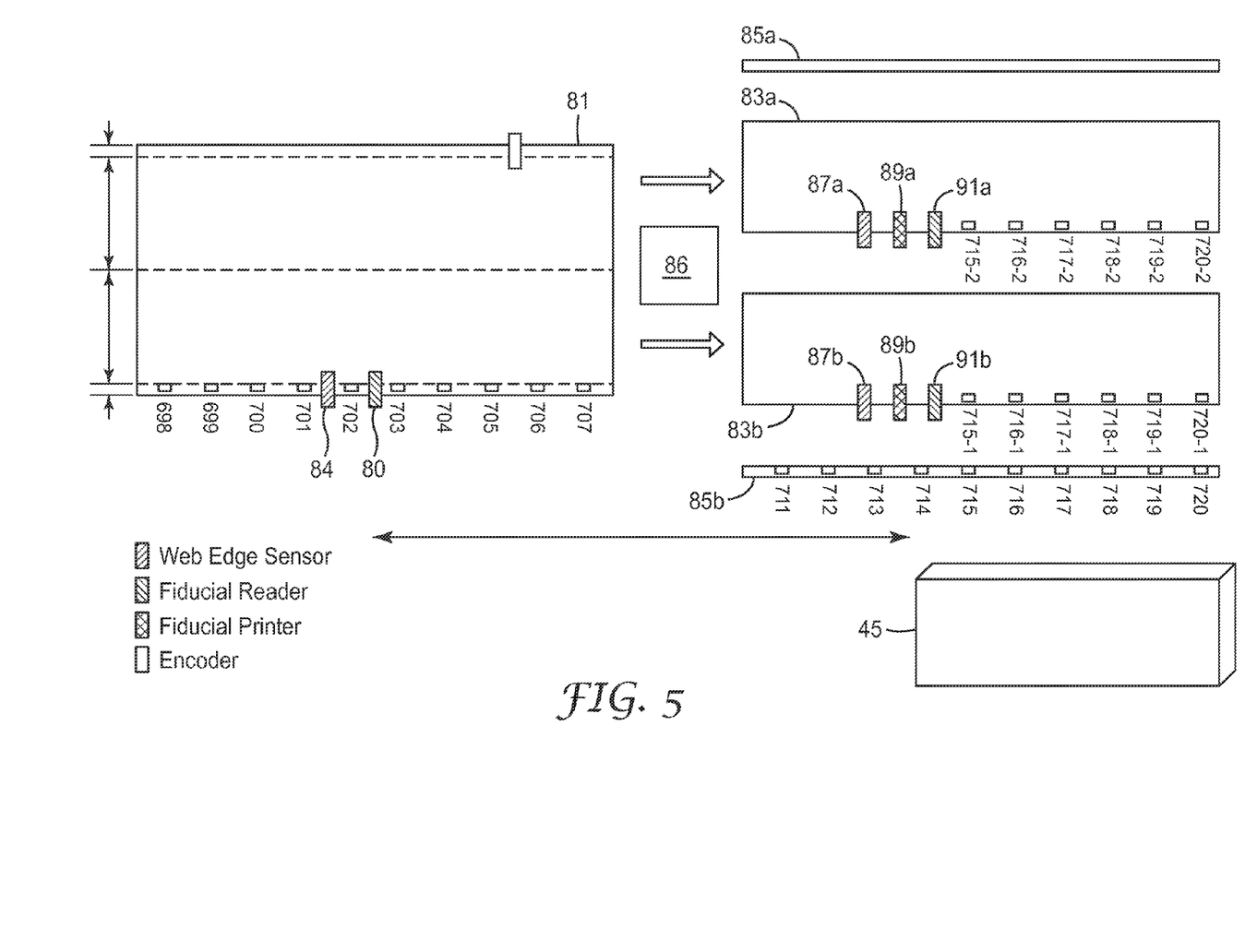
FIG. 5 shows an example of the techniques described herein applied to slit roll processing.

FIG. 5 shows an example of the techniques described herein applied to slit roll processing. In this example, a fiducial reader 80 reads existing fiducial marks on web 81 during the course of processing and outputs signals to provide downweb position information to position monitoring system 45. A web edge sensor 84 may be used to guide fiducial reader 80 with respect to the edge of web 81.

Web 81 is fed into slitter 86 where slitting knives are used to cut the web into slit rolls 83A, 83B and weed rolls 85A, 85B of discard material. Fiducial mark printers 89A and 89B downweb from the slitter may be a known distance D from fiducial mark reader 80 that is upstream from slitter 86.

Conversion processing line 76 includes mechanisms for adding fiducial marks, such as a fiducial ink printer to each individual slit rolls. Position monitoring system 45 uses positional data for the fiducial marks of web 81 as read by upstream fiducial mark reader 80 to compute the positional data associated with each of the marks printed on slit rolls 83A, 83B. Further, position monitoring system 45 may be programmed with the crossweb (transverse) directional position of each slitting knife of slitter 86. In one example, when the downweb or machine direction position of a jumbo fiducial mark on web 81 reaches the distance, "D", from fiducial reader 80, position monitoring system 45 outputs signals causing fiducial printers 89A, 89B to reprint the original fiducial code on each of slit rolls 83A, 83B along with a suffix indicating the unique slit roll, e.g., "−1" and "−2."

Figure 6:
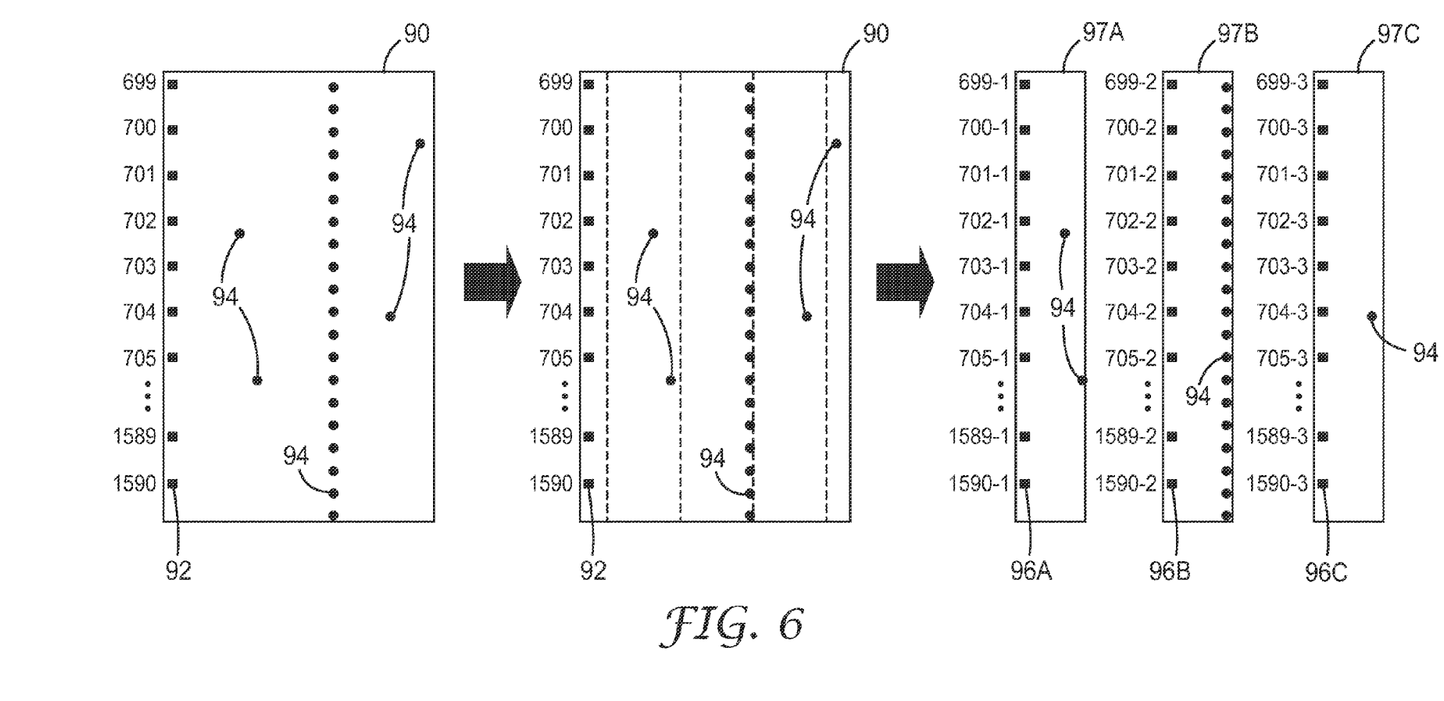
FIG. 6 illustrates maintaining registration and spatial synchronization of anomaly data, including positional information for detected anomalies, between a jumbo web roll and three slit rolls produced therefrom.

FIG. 6 illustrates the re-registration and spatial synchronization of anomaly data, including positional information, between a jumbo web roll and three slit rolls 97A, 97B and 97C produced therefrom. In this example, jumbo web roll 90 includes original fiducial marks 92. Moreover, inspection data for jumbo web roll 90 identifies anomalies 94 at particular downweb and crossweb locations relative to fiducial marks 92. During a subsequent manufacturing operation, jumbo web roll 90 is cut into slit rolls 97A, 97B and 97C. As shown, initial fiducial marks 92 were printed on an edge of web roll 90 and, in this example, are part of the discarded material that is not used for slit rolls 97A-97C. However, in accordance with the techniques described herein, a corresponding set of fiducial marks 96A, 96B and 96C are printed on respective slit rolls 97A, 97B and 97C at positions determined from position information associated with fiducial marks 92. Moreover, positional information for web inspection data from jumbo web roll 90 is recomputed and updated so the anomaly information identifying anomalies 94 present on each of slit rolls 97A, 97B and 97C are spatially relative to the corresponding fiducial marks 96A, 96B and 96C of respective slit roll. That is, in the event the fiducial marks 96A, 96B and 96C and fiducial marks 92 are not printed at the same downweb position, the positional information for anomalies 94 present on each of slit rolls 97A, 97B and 97C may be recomputed for any downweb offset. Moreover, the crossweb positions of the set of anomalies 94 present on each of slit rolls 97A, 97B and 97C may be recomputed to be relative to the corresponding fiducial marks 96A, 96B and 96C of the respective slit roll.

Figure 7:
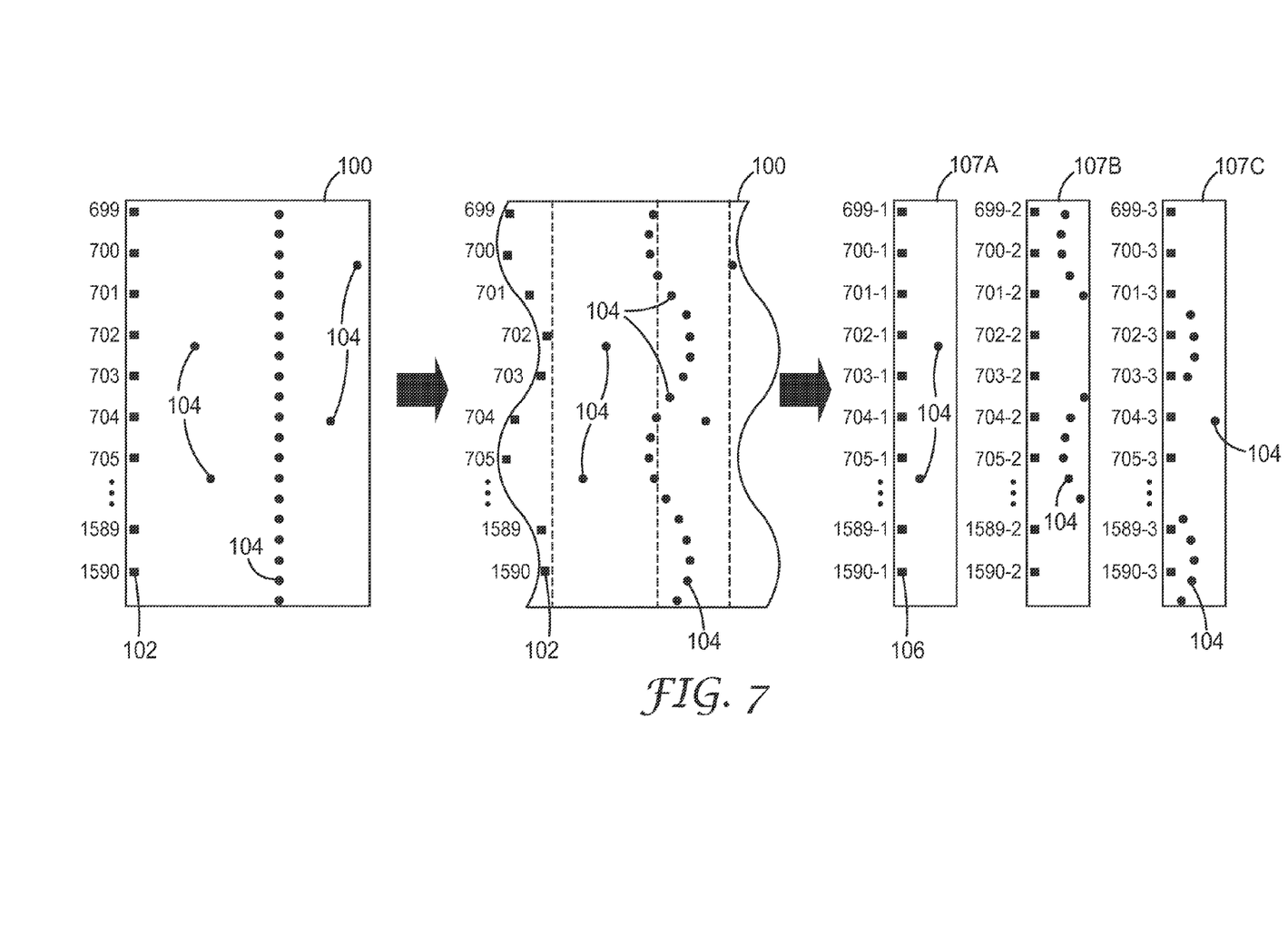
FIG. 7 illustrates another example of re-registration and spatial synchronization of anomaly data between a jumbo web roll and three slit rolls in the presences of web oscillations.

FIG. 7 illustrates the re-registration and spatial synchronization of anomaly data, including positional information, as a jumbo web roll 100 is processed into three slit rolls 107A, 107B and 107C. In this example, oscillations were induced during the wind or unwind operation to reduce the effect of caliper variations in roll formation. The techniques described herein can be utilized with web edge tracking. In this case, when jumbo fiducial marks 102 are read, the crossweb position are monitored during or just prior to slitting. Downweb position information recorded within the anomaly data original captured for web roll 100 is associated with a crossweb offset computed from the current crossweb positions of fiducial marks 102. For example, the crossweb offset for a given anomaly 104 may be interpolated or curve fitted from the crossweb position of the two or more nearest fiducial marks 102 when slitting web 100. The crossweb offset for each anomaly 104 is applied to the position data of the anomaly data to ensure that the data is spatially synchronized for each of the physical webs of slit rolls 107A, 107B and 107C.

Figure 8A:
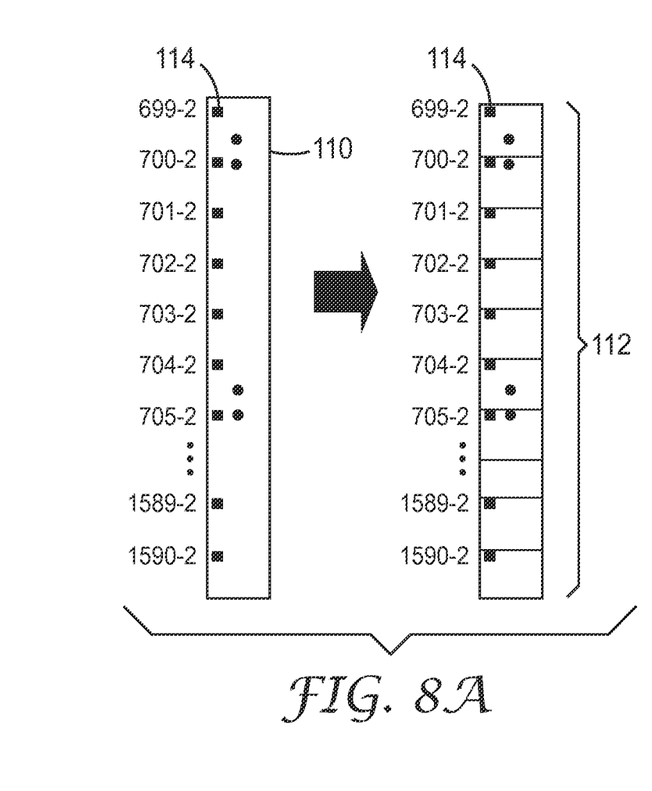
FIGS. 8A and 8B illustrate application of the techniques for tracking individual sheets used for products, which may be useful for monitoring product returns.
Figure 8B:
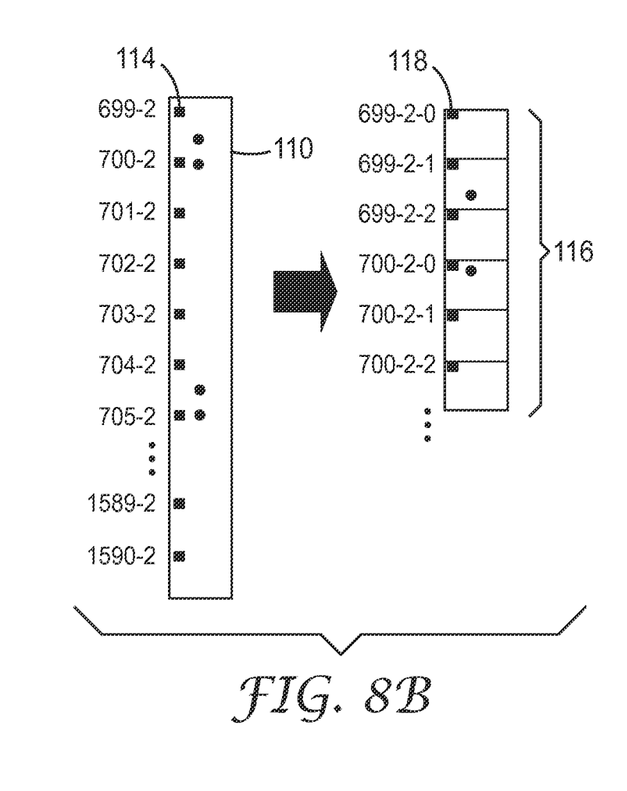

FIGS. 8A and 8B illustrate application of the techniques for tracking individual sheets used for products, which may be useful for monitoring product returns. In the example of FIG. 8A, at least one of fiducial marks 114 is included within each of product sheets 112 and the techniques described herein allow anomaly information from an initial web roll 10 (e.g., a jumbo roll) to be spatially synchronized to individual product sheets 112.

In some cases, product size requirements and downweb spacing between fiducial marks 114 may prevent one of fiducial marks 114 from being included within each cut product sheet 112. For example, in some examples, fiducial marks 114 may be printed at intervals ranging from 1 m to 5 m in the downweb direction. In this example, directly re-registering fiducial marks 114 as described above, not every converted sheet would contain a fiducial mark.

In this case, as shown in FIG. 8B, a cutter or other machine cuts a roll of web material (e.g., a slit roll) into product sheets 116, and the positioning monitoring system inserts additional fiducial marks 118 to ensure coverage for each product sheet 116. For example the additional codes can be inserted during the slit roll converting operation or they can be inserted in an additional operation on the resulting slit rolls before converting into product sheets 116. The new fiducial marks 118 may have an prefix identifier that matches the corresponding fiducial mark within web 114 and may include a suffix designator indicating the unique product, e.g., "−1" and "−2." As such, each fiducial mark may have a first portion having an identifier that matches an identifier for a fiducial mark on jumbo web roll (e.g., "900"), a second portion having an identifier that matches an identifier for a fiducial mark on a slit roll (e.g., "700-2") and a third portion that identifies the particular product sheet 116 within the slit roll of the jumbo roll (e.g., "700-2-0").

Various embodiments of the invention have been described. These and other embodiments are within the scope of the following claims.

The invention claimed is:

1. A system comprising:
   a database that stores anomaly data acquired from a manufactured web, wherein the anomaly data specifies a position of at least one anomaly within a manufactured web relative to a set of fiducial marks on the manufactured web; and
   a conversion processing line that comprises:
   a fiducial mark reader to output position information for the set of fiducial marks on the manufactured web;
   a slitter positioned downweb from the fiducial mark reader to cut the manufactured web into two or more slit rolls of web material;
   a fiducial mark printer to print a set of fiducial marks on the web material of each of the slit rolls; and
   a position monitoring system that maintains spatial synchronization of the anomaly data by computing an updated position for the anomaly relative to the set of fiducial marks printed on the web material of the slit rolls.

2. The system of claim 1,
   wherein the fiducial mark printer prints the set of fiducial marks on the web material of the slit) rolls at substantially the same downweb positions as the set of fiducial marks on the manufactured web, and
   wherein the position monitoring system computes an updated crossweb position for the anomaly relative to a crossweb position of the set of fiducial marks printed on the web material of the slit rolls.

3. The system of claim 2,
   wherein the position monitoring system controls the fiducial mark printer to print a corresponding one of the fiducial marks on the web material of the slit rolls for each fiducial mark on the manufactured web, and
   wherein the position monitoring system controls the fiducial mark printer to print each of the fiducial marks on the web material of the slit rolls to have a first portion that identifies the corresponding fiducial mark on the manufactured web and a second portion that identifies the fiducial mark on the slit roll.

4. The system of claim 1,
   wherein the fiducial mark printer prints the set of fiducial marks on the web material of the slit rolls at a downweb offset from downweb positions of the fiducial marks on the manufactured web, and
   wherein the position monitoring system computes an updated downweb position for the anomaly relative to the downweb position at least one of the fiducial marks printed on the web material of the slit rolls.

5. The system of claim 1, wherein the position monitoring system computes an updated crossweb position for the anomaly relative to a crossweb position for one or more of the fiducial marks printed on the web material of the slit rolls.

6. The system of claim 5, wherein the position monitoring system computes the updated crossweb position for the anomaly by interpolating or curve fitting between the crossweb position of two or more of the fiducial marks printed on the web material of the slit rolls.

7. The system of claim 1, further comprising:
a machine to cut the web material of at least one of the slit rolls into a set of product sheets;
a second fiducial mark printer to print a set of fiducial marks on each of the product sheets, wherein the second fiducial mark printer prints one or more fiducial marks on the product sheets for each fiducial mark on the web material of the slit roll from which the product sheets were cut,
wherein the position monitoring system controls the second fiducial mark printer to print each of the fiducial marks on the product sheets to have a first portion that identifies the corresponding fiducial mark on the manufactured web, a second portion that identifies the corresponding fiducial mark on the slit roll from which the product sheets were cut, and a third portion that identifies the fiducial mark on the product sheet.

8. The system of claim 7, wherein the position monitoring system maintains spatial synchronization of the anomaly data by computing an updated position for the anomaly relative to locations of the set of fiducial marks printed on the product sheets.

9. A method comprising:
storing anomaly data that specifies a position of at least one anomaly within a first web relative a set of fiducial marks on a manufactured web;
transporting the manufactured web through a conversion processing line;
while transporting the manufactured web, detecting position information for the set of fiducial marks on the manufactured web with a fiducial mark reader;
cutting, with a slitter positioned downweb from the fiducial mark reader, the manufactured web into two or more slit rolls of web material;
controlling a fiducial mark printer downweb from the slitter to print a set of fiducial marks on the web material of each of the slit rolls based on the detected position information for the set of fiducial marks on the manufactured web; and
maintaining spatial synchronization of the anomaly data with a position monitoring system by computing an updated position for the anomaly relative to the set of fiducial marks printed on the web material of the slit rolls.

10. The method of claim 9, further comprising:
controlling the fiducial mark printer to print the set of fiducial marks on the web material of the slit rolls at substantially the same downweb positions as the set of fiducial marks on the manufactured web, and
computing, with the position monitoring system, an updated crossweb position for the anomaly relative to a crossweb position of the set of fiducial marks printed on the web material of the slit rolls.

11. The method of claim 10,
controlling the fiducial mark printer with the position monitoring system to print a corresponding one of the fiducial marks on the web material of the slit rolls for each fiducial mark on the manufactured web, and
controlling the fiducial mark printer with the position monitoring system to print each of the fiducial marks on the web material of the slit rolls to have a first portion that identifies the corresponding fiducial mark on the manufactured web and a second portion that identifies the fiducial mark on the slit roll.

12. The method of claim 9,
controlling the fiducial mark printer with the position monitoring system to print the set of fiducial marks on the web material of the slit rolls at a downweb offset from downweb positions of the fiducial marks on the manufactured web, and
computing, with the position monitoring system computes, an updated downweb position for the anomaly relative to the downweb position at least one of the fiducial marks printed on the web material of the slit rolls.

13. The method of claim 9, further comprising computing, with the position monitoring system, an updated crossweb position for the anomaly relative to a crossweb position for one or more of the fiducial marks printed on the web material of the slit rolls.

14. The method of claim 13, further comprising computing, with the position monitoring system, the updated crossweb position for the anomaly by interpolating or curve fitting between the crossweb position of two or more of the fiducial marks printed on the web material of the slit rolls.

15. The method of claim 9, further comprising:
cutting the web material of at least one of the slit rolls into a set of product sheets;
controlling a second fiducial mark printer with the position monitoring system to print a set of fiducial marks on each of the product sheets, wherein the second fiducial mark printer prints one or more fiducial marks on the product sheets for each fiducial mark on the web material of the slit roll from which the product sheets were cut, and wherein the position monitoring system controls the second fiducial mark printer to print each of the fiducial marks on the product sheets to have a first portion that identifies the corresponding fiducial mark on the manufactured web, a second portion that identifies the corresponding fiducial mark on the slit roll from which the product sheets were cut, and a third portion that identifies the fiducial mark on the product sheet.

16. The method of claim 15, further comprising computing, with the position monitoring system, an updated position for the anomaly relative to locations of the set of fiducial marks printed on the product sheets.

* * * * *